United States Patent [19]

Rodder

[11] Patent Number: 4,819,693
[45] Date of Patent: Apr. 11, 1989

[54] FAST OPERATING BISTABLE VALVE

[76] Inventor: Jerome A. Rodder, 775 Sunshine Dr., Los Altos, Calif. 94022

[21] Appl. No.: 859,140

[22] Filed: Apr. 30, 1986

Related U.S. Application Data

[63] Continuation-in-part of Ser. No. 713,088, Mar. 15, 1985, abandoned, which is a continuation-in-part of Ser. No. 508,811, Jun. 28, 1983, abandoned.

[51] Int. Cl.$^4$ ............................................. F16K 31/06
[52] U.S. Cl. .................................. 137/625.4; 251/65; 251/129.05; 251/129.1; 251/129.14
[58] Field of Search ................ 251/65, 129.14, 129.05; 137/625.65

[56] References Cited

U.S. PATENT DOCUMENTS

| | | | |
|---|---|---|---|
| 2,983,278 | 5/1961 | Heintz | 251/137 X |
| 3,245,652 | 4/1966 | Roth | 251/139 |
| 3,379,214 | 4/1968 | Weinberg | 251/65 |
| 3,443,585 | 5/1969 | Reinicke | 251/141 X |
| 3,523,676 | 8/1970 | Barker | 251/141 |
| 3,552,437 | 1/1971 | Blosser, Jr. et al. | 137/625 |
| 3,659,631 | 5/1972 | Rakoske | 251/141 X |
| 3,688,495 | 9/1972 | Fehler et al. | 251/141 X |
| 3,731,880 | 5/1973 | Williams | 251/129.14 X |
| 3,828,818 | 8/1974 | Hunt | 251/141 X |
| 3,865,312 | 2/1975 | Lombard et al. | 251/129.14 X |
| 4,350,319 | 9/1982 | Kawata et al. | 251/65 |
| 4,434,765 | 3/1984 | Eshelman | 251/129.14 X |

FOREIGN PATENT DOCUMENTS

| | | | |
|---|---|---|---|
| 2337886 | 2/1975 | Fed. Rep. of Germany | 251/141 |
| 1497608 | 9/1967 | France . | |
| 2059387 | 5/1971 | France . | |
| 2544834 | 10/1984 | France | 251/65 |
| 208703 | 7/1924 | United Kingdom | 251/137 |

Primary Examiner—Arnold Rosenthal
Attorney, Agent, or Firm—Christie, Parker & Hale

[57] ABSTRACT

A fast operating bistable valve has a movable spherical plug made of magnetic material and a chamber in which the plug is disposed. The chamber has an interior wall shaped to guide the plug along an axis between a first end position and a second end position. A first pole piece made of magnetic material is disposed at the first end position. A first port opens into the chamber such that the plug covers the first port in one end position. A second port opens into the chamber in communication with the first port when the plug is in the other end position. Responsive to a periodic electric current, a first periodic magnetic field of a first given polarity parallel to the axis is generated in the first pole piece to attract periodically the plug to the first end position. The plug is placed in the second end position in the absence of the electric current.

21 Claims, 5 Drawing Sheets

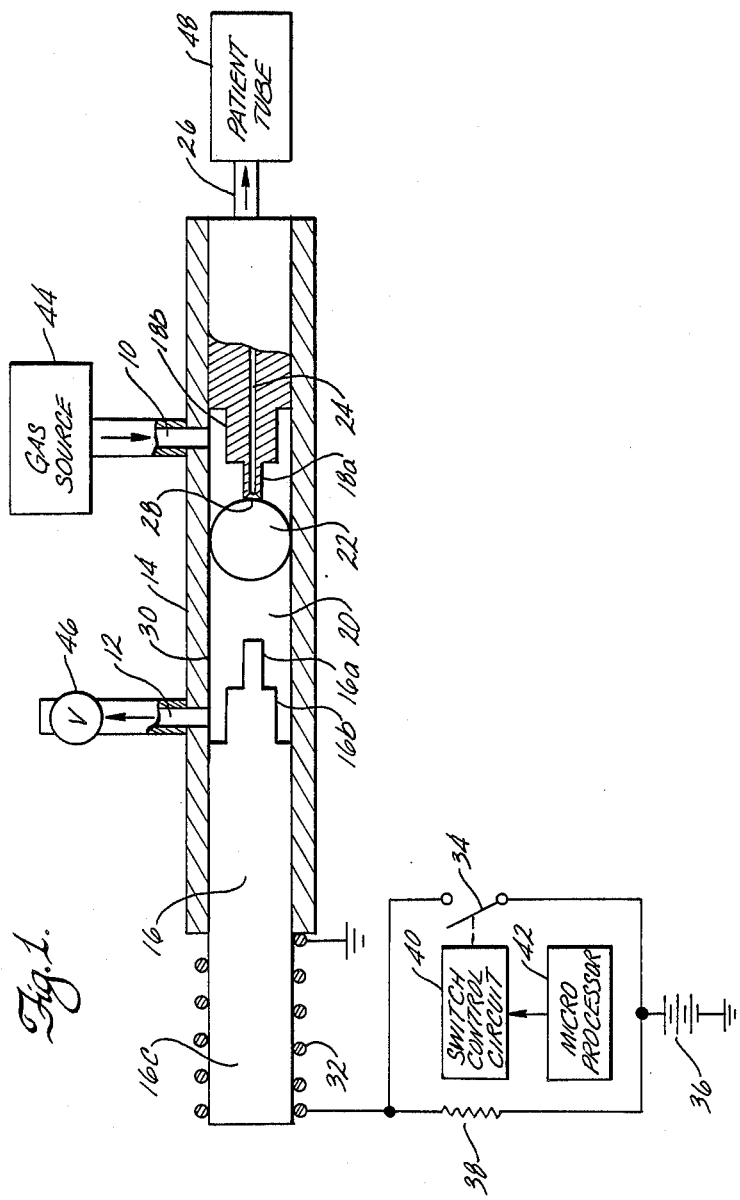

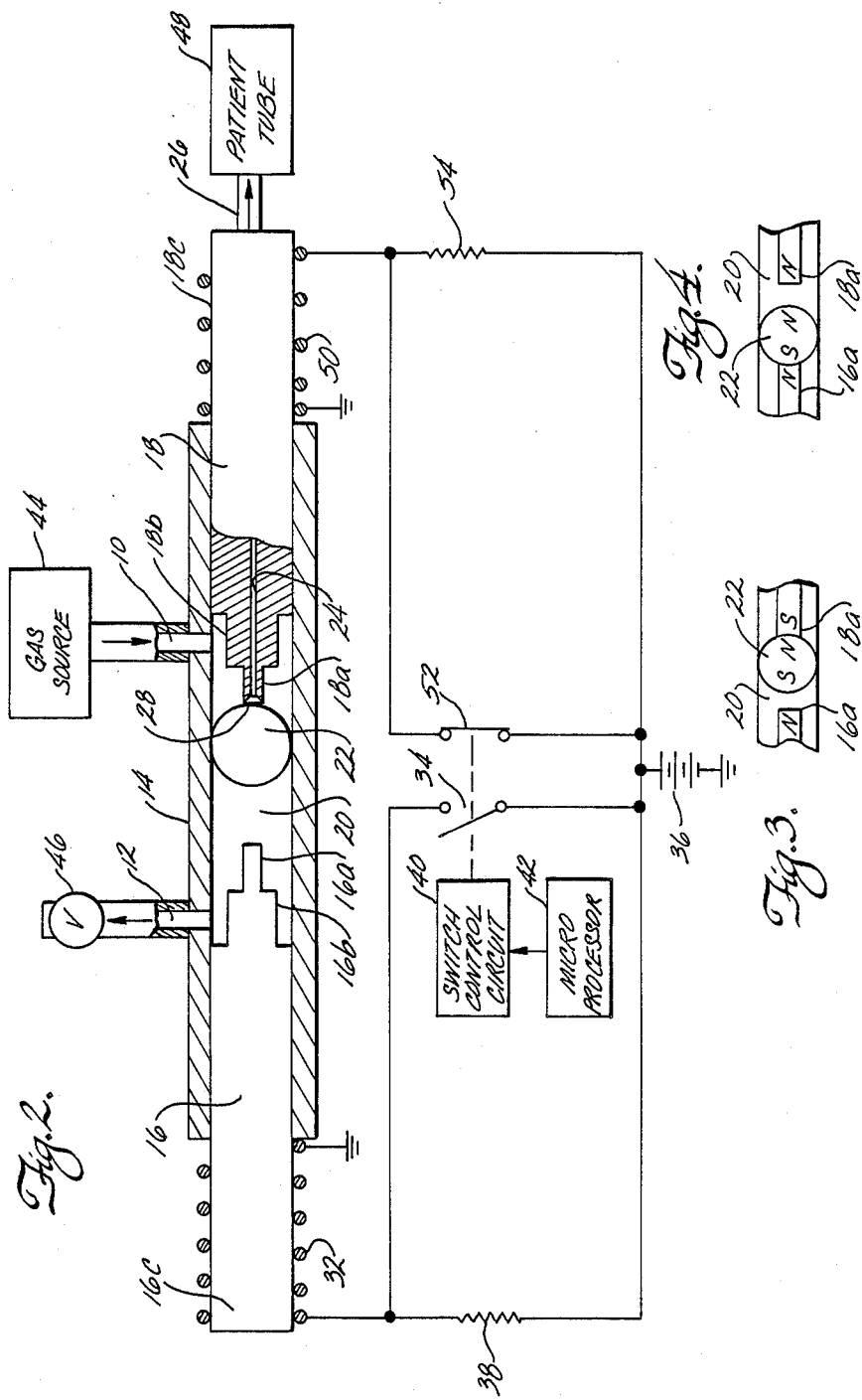

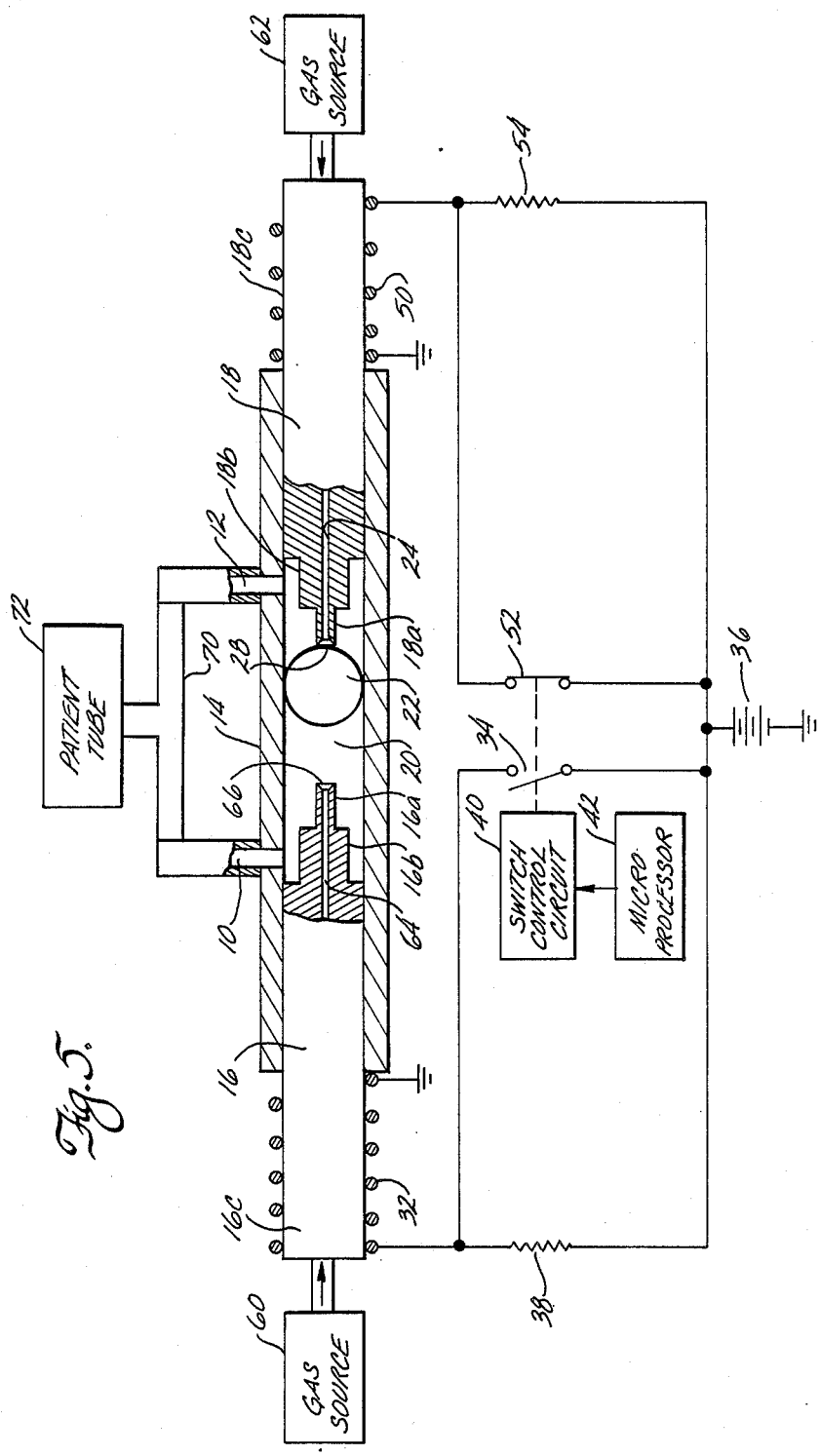

FAST OPERATING BISTABLE VALVE

This is a continuation-in-part of application Ser. No. 713,088, filed Mar. 15, 1985, now abandoned, which is a continuation-in-part of Ser. No. 508,811, filed June 28, 1983, and now abandoned.

BACKGROUND OF THE INVENTION

This invention relates to fluid control and, more particularly, to a fast operating bistable valve particularly useful in precisely controlling gas flow.

There are a number of applications for a valve to control gas flow precisely as a function of the duty cycle of a source of electrical pulses. To respond rapidly to changes in gas flow commands, a fast operating on-off, i.e., bistable, valve is required. Available solenoid valves are too slow operating and short in life expectancy for a number of precision applications such as respirators.

SUMMARY OF THE INVENTION

According to the invention, a fast operating bistable valve has a movable plug made of magnetic material and a chamber in which the plug is disposed. The chamber has an interior wall shaped to guide the plug along an axis between a first end position and a second end position. A first pole piece made of magnetic material is disposed at the first end position. A first port opens into the chamber such that the plug covers the first port in one end position. A second port opens into the chamber in communication with the first port when the plug is in the other end position. Responsive to a periodic electric current, a first periodic magnetic field of a first given polarity parallel to the axis is generated in the first pole piece to attract periodically the plug to the first end position. The plug is placed in the second end position in the absence of the electric current. The plug can move rapidly between the first and second end positions responsive to the electric current, thereby permitting rapid change in the gas flow in response to changes in the duty cycle of the command signal.

In one embodiment, the plug is placed in the second end position by means of a second pole piece made of magnetic material at the second end position. Responsive to an electric current, a second magnetic field of a second given polarity parallel to the axis is generated in the second pole piece to attract periodically the plug to the second end position. While generating the second magnetic field in the second pole piece, there is applied to the first pole piece a magnetic field of polarity opposite to the second given polarity and of a magnitude to induce in the plug a magnetic field smaller than the magnetic field induced therein by the second magnetic field. Similarly, while generating the first magnetic field in the first pole piece, there is applied to the second pole piece a magnetic field of polarity opposite to the first given polarity and of a magnitude to induce in the plug a magnetic field smaller than the magnetic field induced therein by the first magnetic field. In each case, the applied magnetic field serves to repel the plug, thereby assisting the attraction of the plug to the other pole piece.

A feature of the invention is a spherical plug which discourages binding and facilitates rapid movement between the end positions of the chamber without alignment problems.

BRIEF DESCRIPTION OF THE DRAWINGS

The features of specific embodiments of the best mode contemplated of carrying out the invention are illustrated in the drawings, in which:

FIG. 1 is the schematic diagram of one embodiment of the invention;

FIG. 2 is a schematic diagram of another embodiment of the invention;

FIGS. 3 and 4 are diagrams of the pole pieces and plug, illustrating the attraction-repulsion operation of the valve of FIG. 2;

FIG. 5 is a schematic diagram of still another embodiment of the invention;

DETAILED DESCRIPTION OF THE SPECIFIC EMBODIMENTS

Figure 6:
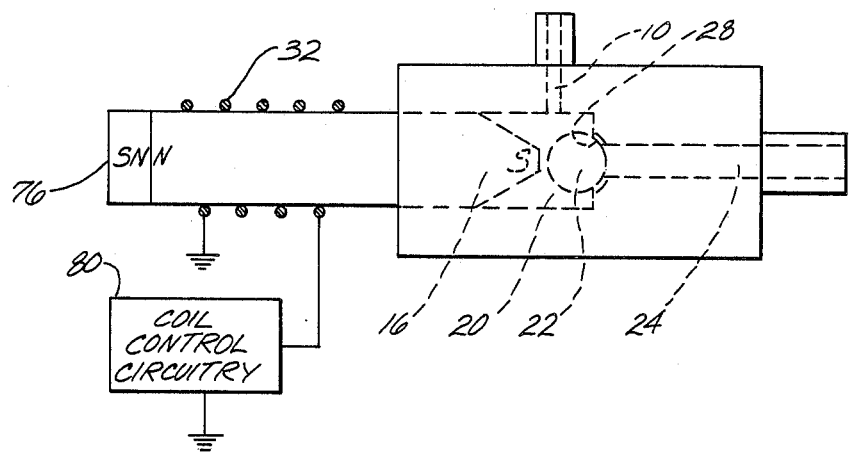
FIG. 6 is a schematic diagram of yet another, and presently preferred, embodiment of the invention.

In FIG. 1, fluid ports 10 and 12 open into the interior of a tubular, open ended valve body 14, which is made of nonmagnetic material such as aluminum. An end piece 16 made of magnetic material, such as iron, fits in one open end of valve body 14 and an end piece 18 fits in the other open end of valve body 14. In this embodiment, piece 18 is made of nonmagnetic material. The interior end surfaces of end pieces 16 and 18 and the cylindrical interior side surface of valve body 14 together define a chamber 20 within which a freely movable, close fitting spherical plug 22 made of magnetic material, such as iron, can move back and forth along a path defining its stroke. The clearance between plug 22 and the interior surface of valve body 14 is very small, typically of the order of 0.001 to 0.0005 of an inch. The interfaces between end pieces 16 and 18 and the interior surface of valve body 14 are sealed in a conventional manner, for example by O-rings not shown. In chamber 20, end piece 16 has a distal portion 16a of small diameter and a connecting portion 16b of intermediate diameter between distal portion 16a and the remainder of piece 16. End piece 18 has a distal portion 18a of small diameter and a connecting portion 18b of intermediate diameter between distal portion 18a and the remainder of end piece 22. Distal portion 18a has a concave semi-spherical seating surface 28 that matches the radius curvature of plug 22. The stroke of plug 22 is much smaller than prior art solenoid values, i.e., typically of the order of several one-thousandths of an inch, which permits rapid switching of valve state between open and closed. Typically, the stroke of plug 22 is about at least an order of magnitude smaller than diameter, i.e., about 0.1 or less. A port 24 extends axially along the full length of end piece 18 from chamber 20 to the exterior of valve body 14. Port 12 opens into chamber 20 adjacent to connecting portion 16b and port 10 opens into chamber 20 adjacent to connecting portion 18b.

A portion 16c of end piece 16 extends outside valve body 14. An electric coil 32 is wrapped around portion 16c. One end of coil 32 is grounded. The other end of coil 32 is connected through a switch 34 to the positive terminal of a battery 36. The negative terminal of battery 36 is grounded. A resistor 38 is connected in parallel with switch 34 to permit discharge of coil 32 when switch 34 opens. Switch 34 is opened and closed by a switch control circuit 40 under the control of a microprocessor 42.

In operation, the described valve is bistable. When switch 34 closes, the current flowing through coil 32 generates a magnetic field that attracts plug 22 to distal portion 16a; in this state, the surface of plug 22 abuts end piece 16 to open the valve and provide a free flow path between ports 10 and 24. End piece 16 thus serves as a magnetic pole piece that attracts plug 22 to one end position in chamber 20 when switch 34 is closed. By virtue of the close fit of plug 22 with the interior side surface of body 14 and the small opening, or no opening, of port 12, the space between end piece 16 and plug 22 has small enough venting to the atmosphere to produce between end piece 16 and plug 22 a buildup of the pressure of the gas fed to the valve through port 10. When switch 34 opens, gas pressure in chamber 20 between plug 22 and end piece 16 drives plug 22 into abutment with distal portion 18a. In this state, the surface of plug 22 fits snuggly with surface 28 to substantially seal port 24. To permit gas pressure to return plug 22 to seating surface 28 as described, port 12 is either completely closed or has only a very small opening, vis-a-vis, port 24, depending on the pressure of the gas supplied to the valve and the frequency of operation of switch 34. Alternately, instead of gas pressure return, a compression spring could be disposed in chamber 20 between end piece 16 and plug 22, thereby normally urging plug 22 against seating surface 28 of distal portion 18a.

Although the described valve has many applications, it serves as a respirator in the embodiment of FIG. 1. The disclosures of U.S. Pats. Nos. 4,333,453 and 4,259,968 are incorporated fully herein by reference. Specifically, with reference to FIG. 4 of U.S. Pat. No. 4,333,453, issued June 8, 1982, the valve of FIG. 1 is substituted for valve 65. A gas source 44, which supplies oxygen, is connected to port 10. An adjustable needle valve 46 is connected between port 12 and the atmosphere. (Needle valve 46 is opened sufficiently so there is just enough gas pressure to return plug 22 reliably to seating surface 18 when switch 34 is open, thereby minimizing the force required to unseat plug 22 from surface 28 when switch 34 closes.) A patient tube 48 is connected to port 24. The volume of gas supplied from source 44 to a patient through the described valve and patient tube 48 depends upon the duty cycle of switch control circuit 40, which is adjusted on an ongoing basis by microprocessor 42 so as to maintain a desired flow rate. The term "duty cycle" means herein the ratio of pulse duration to pulse period. In general, microprocessor 42 calculates the desired flow rate from data received from one or more sensors such as, for example, a flowmeter and/or a pressure sensor and generates periodic pulses with a duty cycle that varies so as to maintain the desired flow rate. Needle valve 46 provides pressure relief within chamber 20. Needle valve 46 is preferably adjusted without the spring (if used) and without a magnetic field to provide sufficient venting to the atmosphere so plug 22 is suspended between distal portions 16a and 18a. This minimizes the magnetic field and spring force required to operate the valve; if needle valve 46 is open too far, plug 22 will abut distal portion 16a and, if open too little, distal portion 18a.

In the embodiment of FIG. 2, the components common to the embodiment of FIG. 1 bear the same reference numerals. In this embodiment, there is no spring or pressure induced plug return. End piece 18 is made of magnetic material and has a portion 18c that extends outside body 14. An electric coil 50 is wrapped around portion 18c in the same direction of rotation as coil 32 viewed from one end of valve body 14. The end of coil 50 adjacent to valve body 14 is grounded. The other end of coil 50 is connected by a switch 52 to the positive terminal of battery 36. A resistor 54 is connected in parallel with switch 52 to permit discharge of coil 50 when switch 52 opens. The direction in which coils 32 and 50 are wound and the direction of current flow therethrough are such that the resulting magnetic field generated by coils 32 and 50 have opposite polarity, i.e., if a north pole is produced at distal portion 16a by coil 32, then a north pole is also produced at distal portion 18a by coil 50. Switch 52 is closed when switch 34 is open, and vice versa.

In operation, responsive to switch control circuit 40, switches 34 and 52 alternately open and close. When switch 34 closes and switch 52 opens, the current flowing through coil 32 generates a magnetic field in end piece 16 that attracts plug 22 to distal portion 16a. When switch 34 opens and switch 52 closes, the current flowing through coil 50 generates a magnetic field in end piece 18 that attracts plug 22 to distal portion 18a. Thus, plug 22 shuttles back and forth between distal portion 16a and distal portion 18a at a frequency of as high as 100 to 200 Hz. As in the embodiment of FIG. 1, the volume of gas that reaches patient tube 48 depends upon the switch duty cycle. The greater the percentage of time that switch 34 is closed, vis-a-vis, switch 52, the greater is the volumetric flow rate through the described valve to the patient from source 44. Precise metering of gas and rapid change in gas flow rate can thus be achieved. Pressure relief to chamber 20 is provided by port 12 in conjunction with needle valve 46, which is adjusted without application of magnetic fields as described in connection with FIG. 1.

A feature of the invention incorporated in FIG. 2 is the provision of an assisting magnetic field by the coil (32, 50) associated with the open switch (34, 52). This assisting magnetic field is generated by virtue of the continuing circuit path through the parallel resistor (38, 54) when the corresponding switch (34, 52) is open. Consider first the magnetic field produced by coil 32 when switch 34 closes. In the absence of an assisting magnetic field generated by coil 50, there would be a north pole at distal portion 16a, a south pole induced in the adjacent region of plug 22, a north pole induced in the opposite region of plug 22, and a south plug induced at distal portion 18a, as illustrated in FIG. 3. As a result of the induced magnetism, plug 22 would be attracted to distal portion 18a rather than distal portion 16a, which would inhibit movement of plug 22 into abutment with distal portion 16a. This probem is overcome by the small residual current that flows through resistor 54 into coil 50 when switch 52 opens. Such residual current produces in end piece 18 a magnetic field having a polarity to repel plug 22, thereby assisting its movement into abutment with distal portion 16a, as illustrated in FIG. 4. The magnetic field produced in end piece 18 by the residual current is sufficiently small to induce in plug 22 a magnetic field smaller than the magnetic field induced in plug 22 by the magnetic field generated by coil 32. As a result, distal portion 18a and the adjacent region of plug 22 have the same magnetic polarity, e.g., both are north poles, so that plug 22 is repelled by distal portion 18a. Similarly, when switch 34 opens and switch 52 closes, a residual current flows in coil 32 to assist the movement of plug 22 from distal portion 16a to distal portion 18a. The magnetic field generated by this current is likewise sufficiently small to induce in plug 22 a magnetic field smaller than the magnetic field induced therein by the magnetic field generated in end piece 18 by coil 50. Typically, the residual current is of the order of 5% of the current flowing when the switch (34, 52) is closed.

Instead of generating a magnetic field by means of a residual current in one of the coils (32, 50) when its corresponding switch (34, 52) is open, the assisting magnetic field could be produced by permanent magnets.

The valve of FIG. 2 is capable of precisely controlling the volumetric gas flow from port 10 to port 24 and responds rapidly to changes in commands issued by microprocessor 42. Typically, the frequency of operation of switch control circuit 40 could be of the order of 100 to 200 Hz because of the small distance of travel of plug 22, typically of the order of several thousandths of an inch between distal portions 16a and 18a.

Although it is preferable for the residual current provided by the parallel resistor (38, 54) to be of the same polarity as the actuating current passing through the switch (34, 52), because less energy needs to be stored in the coils (32, 50) and the circuit implementation is simpler, the residual current and the resulting assisting magnetic field could be of the opposite polarity from the operating current and the resulting magnetic field. The important polarity requirement is between the operating magnetic field of one end piece and the assisting magnetic field of the other end piece, which must be of opposite polarity so as simultaneously to attract and to repel plug 22.

In FIG. 5, an embodiment of the invention functions to mix together two different gases from a gas source 60 and a gas source 62. In this embodiment, the components in common with the embodiment of FIG. 2 bear the same reference numerals. A port 64 extends axially along the full length of end piece 16 from chamber 20 to the exterior of body 14. Distal portion 18a has a semi-spherical seating surface 66 matching the curvature of plug 22 where the interior end of port 64 opens into chamber 20. Gas source 60 is connected to port 64 and gas source 62 is connected to port 24. Ports 10 and 12 are coupled by a Y-connection 70 to a patient tube 72 or other gas receiver. The ratio of the gas from source 60 to the gas from source 62 in the gas mixture applied to patient tube 72 depends upon the proportion of the time plug 22 abuts distal portion 16a versus the proportion of the time plug 22 abuts distal portion 18a, which in turn depends upon the duty cycle of switch control circuit 40.

In FIG. 6, chamber 20 is cylindrical and has a substantially larger diameter than plug 22. A permanent magnet 76 is mounted on the exterior extremity of end piece 16. Inside chamber 20, end piece 16 tapers to a flat surface at its interior extremity. As a result of the large diameter of chamber 20, its walls do not serve to guide plug 22 as it shuttles back and forth during operation. The only appreciable wear to plug 22 occurs as it engages seating surface 28. Magnet 76 produces a substantially smaller magnetic field than coil 32. Magnet 76 is polarized opposite to the polarization of end piece 16 when current flows through coil 32. For example, if the current flow through coil 32 produces a north pole at the extremity of end piece 16 adjacent to magnet 76, the abutting surface of magnet 76 has a north pole and the remote surface has a south pole, as illustrated in FIG. 6. As a result, when current flow through coil 32 is terminated, the magnetic field of magnet 76 assists, i.e., accelerates, the transition of plug 22 from end piece 16 to seating surface 28 in the manner described in connection with FIGS. 2, 3, and 4. The tapering of the internal extremity of end piece 16 concentrates the magnetic field in the region occupied by plug 22, thereby increasing the efficiency of the applied energy. Typically, the included angle of taper is of the order of 60° and the flat interior extremity of end piece 16 is about one-half the diameter of plug 22. Coil control circuitry 80 represents elements 34 through 42 in FIG. 1. In operation, when current flows through coil 32, the magnetic field generated thereby attracts plug 22 pulling it into abutment with the tapered extremity of end piece 16. When current flow through coil 32 is interrupted, the pressure drop from port 10 to port 24, assisted by the magnetic field of permanent magnet 76, draws plug 22 away from end piece 16 against seating surface 28 to form a metal-to-metal seal therebetween. Typically, fluid pressure in port 10 is 10 to 15 psi higher than that in port 24, the stroke, i.e., length of travel of plug 22 is less than 0.010 inch, and the diameter of ball 22 is about 3/32 inch. Most efficient concentration of the magnetic field results when the extremity of the taper of end piece 16 is about one-half of the diameter of plug 22.

In some applications such as the respirator described above, it is important that very little leakage occur when the valve is closed. It has been discovered that the ratio of diameter of port 24 to diameter of plug 22 is important for establishing a good seal between plug 22 and seating surface 28. If the diameter of port 24 is too small, plug 22 rolls around continuously on seating surface 28, never seating completely. As a result, a slight leakage occurs when the valve is closed. When the diameter of port 24 is sufficiently large, however, i.e., the diameter ratio of port 24 to plug 22 being greater than about 0.75, plug 22 seats squarely on seating surface 28 without rolling movement. In a typical example, with a diameter of 3/32 inch for plug 22, the diameter of port 24 is 0.081 inch. Seating surface 28 can be formed by end milling with a circular cutter having the same diameter as plug 22. Typically, the cutter travel in an axial direction is 0.004 to 0.005 inch beginning from the point of contact of the cutter with the edge of the hole from which seating surface 28 is formed. After cutting the seating surface, it is lapped with a fine abrasive and a ball having the same diameter as plug 22 to smooth the seating surface.

Figure 7:
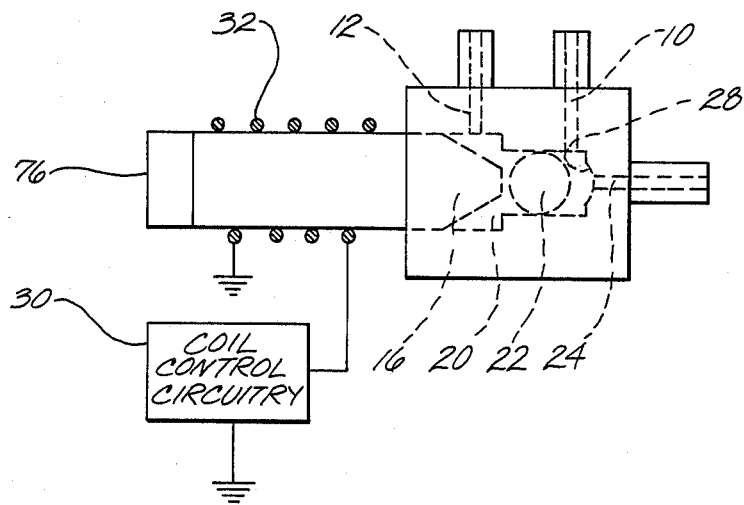
FIG. 7 is a schematic diagram of a modification of the embodiment of FIG. 6.

FIG. 7 shows a modification of the valve of FIG. 6, in which chamber 20 has a small diameter portion into which port 24 opens and a large diameter portion in which the interior extremity of end piece 16 lies. Port 10 opens into the small diameter portion and port 12 opens into the large diameter portion. Port 24 is smaller than in FIG. 6. The clearance between the small diameter portion and plug 22 is small, i.e., of the order of 0.001 inch. Needle valve 46 (FIG. 1) or a pressure regulator is connected to port 12 so the pressure in port 12 is slightly larger than the pressure in port 10, e.g., of the order of 15 psi larger. Since it is the pressure difference between ports 12 and 10 rather than between ports 10 and 24 that closes the valve, i.e., seats plug 22 on seating surface 28, this modification is suitable for high-pressure application. For example, the pressure in port 12 can be 100 psi, the pressure in port 10 can be 85 psi, and port 24 can be near ambient pressure; the magnetic field produced by coil 32 must only overcome a 15 psi pressure difference rather than an 85 psi pressure difference as would be required in the embodiment of FIG. 6.

Figure 8:
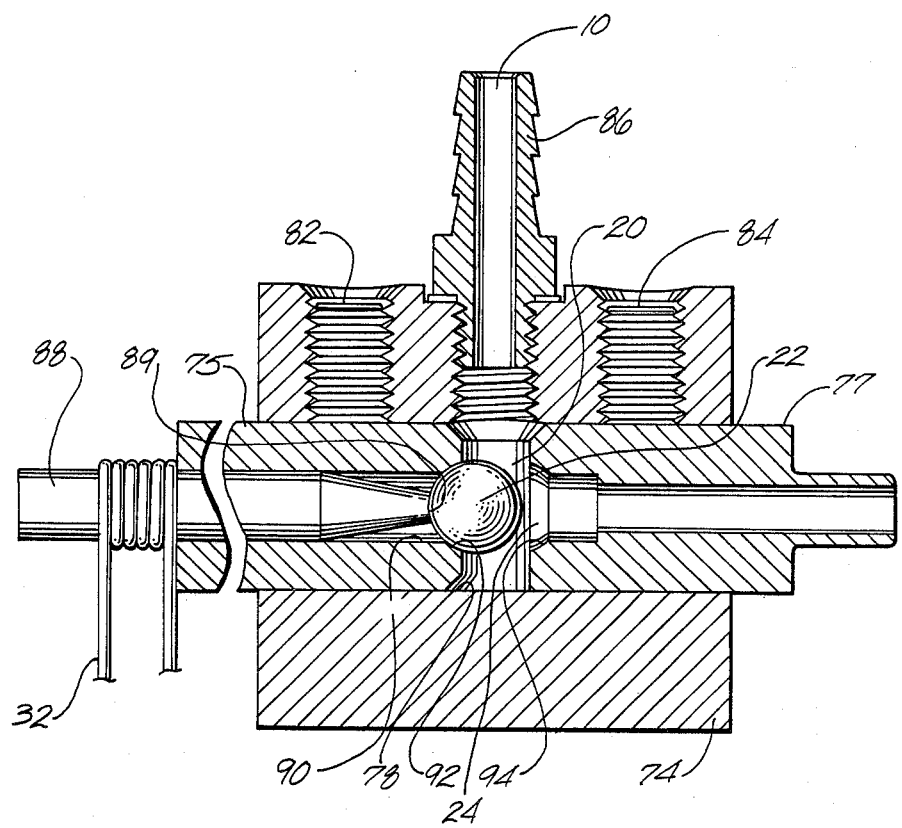
FIG. 8 is a schematic diagram of yet another embodiment of the invention.

In FIG. 8, a chamber 20 is defined by a block-shaped body 74, a cylindrical end piece 75, and a cylindrical end piece 77. End pieces 75 and 77 are preferably made of a hard wear-resistant magnetic material. End pieces 75 and 77 are disposed in closely spaced relationship in a bore 78 passing through body 74. Set screws 82 and 84 secure end pieces 75 and 77, respectively, in place after their spacing has been adjusted. Port 10 is formed in a threaded fitting 86, which engages a threaded bore in body 74 intersecting bore 78. Plug 22 is a sphere disposed between end pieces 75 and 77. The distance of travel, i.e., stroke, of plug 22 between end pieces 75 and 77 is extremely small, i.e., less than 0.03 times the diameter of plug 22. This spacing is greatly exaggerated in FIG. 8 for the purpose of illustration. A cylindrical, axially adjustable pole piece 88 made of magnetic material is disposed in a bore 90 through end piece 75. End pieces 75 and 77, plug 22, and pole piece 88 could be made from a magnetic material such as M-2 tool steel, because of the hardness and resistance to wear of such material. Other than plug 22, pole piece 88, and end pieces 75 and 77, the other parts of this embodiment are nonmagnetic. Port 24 is formed by a bore through end piece 77.

The inner opening of bore 90 has a concave semi-spherical seating surface 92. The inner opening of port 24 has a concave semi-spherical seating surface 94. The curvature of both seating surfaces matches the curvature of the spherical plug. (The width of seating surfaces 92 and 94 is exaggerated for the purpose of illustration.) Preferably, the ratio of the diameter of port 24 (or seating surface 94) to that of plug 22 is as set forth in connection with FIG. 6, i.e., greater than about 0.75. If the ratio is less, the plug has a tendency to roll around in the seat. The less the plug rolls around, the faster the valve closes, the more secure the seal is, and the smaller is the probability of leakage. The seating surfaces are formed as described in connection with FIG. 6.

Magnetic pole piece 88 is tapered at its interior end 89 and curved to match the curvature of plug 22. The tapering concentrates the magnetic field so that less power is needed to attract the plug to magnetic pole piece 88 against the fluid flow pushing the plug toward port 24. The position of pole piece 88 is adjusted by axial movement within bore 90 until the end of pole piece 88 just touches plug 22 when plug 22 is seated on seating surface 92.

When the plug is seated on surface 92 at one end position, it touches the tapered end of magnetic pole piece 88. The ratio of the diameter of the tapered end of pole piece 88 to the plug diameter is about 0.5 in the preferred embodiment; however, other ratios may also be suitable. Surface contact between the plug and the magnetic pole piece strengthens the magnetic force between the two objects without resulting in undue wear to either the plug or the pole piece.

The valve is typically cycled over fifty million times so any point contact would necessarily result in significant wear. It was found that after a million cycles the flat end of pole piece 16 shown in FIG. 6 was dented from the hammering of the plug. The denting occurred no matter how hard a steel was used. The denting of the pole piece increased the stroke of the plug, thus increasing the flow rate through the valve. When the embodiment shown in FIG. 6 was modified to include the seating surface and to eliminate tapering of the rod, the valve did not operate as well, possibly because insufficient magnetic field was created to attract the plug.

It is very important that wear in the valve be minimized, since even a small change in the plug stroke affects the flow rate through the valve. Wear cannot be minimized through lubrication of the valve parts, since any lubricant would contaminate the liquid or gas passing through the valve and render it unsuitable for medical purposes. Consequently, wear can only be minimized by reducing or eliminating point contact between the moving parts and establishing surface contact over a relatively large surface area instead.

The best results are obtained with a combination of a seating surface and a tapered pole piece as shown in FIG. 8. This embodiment reduces the flow rate drift by about 96%. The impact between plug 22 and the tapered end surface of pole piece 88 is very slight: the greatest part of the impact is absorbed by the larger area of seating surface 92.

The wear to seating surfaces 92 and 94 is minimized by using magnetic material for end pieces 75 and 77 because materials having magnetic properties tend to be harder and to have more wear resistance than non-magnetic materials. Non-magnetic ceramic seats were found to be unsatisfactory due to pitting of the seat caused by the impact of the plug; moreover, the abrasive nature of the ceramic resulted in wear to the plug.

The valve described in connection with FIG. 8 can be employed to control the flow of liquids or gases; it is particularly advantageous in a gas environment.

No restrictions are used either upstream or downstream when gas is flowing through the valve. It is important that the valve close and open in a few milliseconds and that the flow rapidly reach its equilibrium state. It should be noted, however, that due to the extremely short stroke and large plug diameter even in the open position, the plug partially obstructs flow through the valve. This partial obstruction aids in the quick response time of the plug to changes in the current and permits precise control over the flow rate by adjusting the stroke, i.e., the position of end piece 75 and/or 77. The axes of bore 90 and the bore forming port 24 are preferably aligned to an accuracy of 0.0002 inch or better. The distance between the first and second end positions, and consequently the length of the stroke of the plug, is adjusted by set screws 84 in valve body 74. The valve stroke is extremely short, preferably less than 0.03 times the ball diameter. The maximum flow rate can be more easily adjusted when the stroke is short and the valve response time is faster.

The maximum flow rate is adjusted to a desired value during manufacture. A plurality of valves with digitally weighted flow rates can then be used under computer control. For example, if the weighted flow rates are 1, 2, 4, 8 and 16, any digital flow rate valve between 0 and 31 can be obtained. With computer control, if a single valve is used, the average flow, which is of course less than the maximum flow, can be controlled by adjusting the ratio of the time the valve is in an open state to the time the valve is in a closed state. In either case the state of the valve is controlled by applying binary signals to coil 32.

It is preferred that plug 22 be spherical as shown, because plug 22 can therefore move freely between the ends of chamber 20 without necessity for guidance means, which would introduce further wear on the moving parts. If guidance means are provided, and the resulting wear can be tolerated, the plug could be cylindrical in shape with spherical seating surfaces on each end that match seating surfaces 92 and 94. Alternatively, seating surfaces 92 and 94 could be conical and plug 22 could be a cylinder with matching conical ends.

The described embodiments of the invention are only considered to be preferred and illustrative of the inventive concept; the scope of the invention is not to be restricted to such embodiments. Various and numerous other arrangements may be devised by one skilled in the art without departing from the spirit and scope of this invention. For example, the described valve can be employed to control the flow of liquid instead of gas and can be utilized for many applications other than those disclosed. Although it is preferable for the plug to be spherical so as to provide a single band of contact with the interior surface of valve body 14, which reduces the possibility of the plug binding and reduces friction, the plug could have other shapes such as, for example, cylindrical or tapered at its ends. As used in the claims, the term "circumferential edge" refers to the inner opening of bore 90, on which concave semispherical seating surface 92 is formed.

What is claimed is:

1. A fast-operating, bistable valve comprising:
 a body in which a chamber is formed, the chamber having first and second ends;
 a spherical plug made of magnetic material disposed in the chamber;
 a bore opening into the chamber at the first end, the bore having a circumferential edge that forms a first seating surface having a curvature that matches the curvature of the plug;
 a tapered pole piece made of magnetic material disposed in the bore such that the end of the pole piece contacts the plug when the plug is seated on the first seating surface, leaving between the pole piece and the first seating surface an area of non contact with the plug;
 a first port opening into the chamber at the second end in axial alignment with the bore to form a second seating surface having a curvature that matches the plug;
 a second port opening into the chamber so as to communicate with the first port when the plug unseats from the second seating surface;
 a source of electric current;
 means responsive to the electric current for generating a magnetic field in the pole piece to attract the plug to the first end of the chamber and seat the plug on the first seating surface; and
 means in the absence of the magnetic field for seating the plug on the second seating surface at the second end of the chamber.

2. The valve of claim 1 in which the distance between the first and second ends of the chamber is such that the distance of travel of the plug therebetween is less than 0.03 times the diameter of the sphere.

3. The valve of claim 1, in which the tapered end of the pole piece has a curvature matching that of the sphere.

4. The valve of claim 3, in which the tapered end of the pole piece is so positioned relative to the first seating surface that the first seating surface absorbs more of the impact of the plug than the tapered end of the pole piece.

5. The valve of claim 1, in which the diameter of the first port is greater than about 0.75 times the diameter of the plug.

6. The valve of claim 5, in which the first seating surface and the second seating surface are made of hard wear-resistant magnetic material.

7. A fast-operating, bistable valve comprising:
 a chamber having a first end and a second end;
 a moveable spherical plug made of magnetic material disposed within the chamber;
 a pole piece made of magnetic material at one end of the chamber;
 a first port opening into the chamber at one end to form a seating surface having a curvature that matches the curvature of the plug, the ratio of the diameter of the first port to the diameter of the plug being greater than about 0.75 and the seating surface being formed from a hard wear-resistant material;
 a second port opening into the chamber so as to communicate with the first port when the plug unseats from the seating surface;
 a source of electric current;
 means responsive to the electric current for generating a magnetic field that attracts the plug to the pole piece; and
 means for driving the plug to the end opposite the pole piece in the absence of the magnetic field.

8. The valve of claim 7, in which the pole piece has an end with a spherical seating surface that matches the curvature of the plug.

9. The valve of claim 8, in which the end of the pole piece is tapered.

10. A fast-operating, bistable valve comprising:
 a chamber having a first end and a second end;
 a moveable spherical plug made of magnetic material disposed within the chamber;
 a pole piece made of magnetic material at one end of the chamber;
 a first port opening into the chamber at one end to form a seating surface having a curvature that matches the curvature of the plug;
 a second port opening into the chamber so as to communicate with the first port when the plug unseats from the seating surface;
 a source of gas under pressure connected to one port without flow restriction therebetween;
 a gas receiver connected to the other port without flow restriction therebetween;
 a source of electric current;
 means responsive to the electric current for generating a magnetic field that attracts the plug to the pole piece; and
 means for driving the plug to the end opposite the pole piece in the absence of the magnetic field;
 the distance of travel of the plug between the ends of the chamber being sufficiently small that the plug restricts flow through the first port when the plug is at the end opposite the pole piece.

11. The valve of claim 10 additionally comprising a bore aligned with the first port at the other end of the chamber to form a seating surface having a curvature that matches the sphere, the pole piece being positioned within the bore such that the seating surface on its end contacts the sphere when seated on the seating surface of the bore.

12. The valve of claim 7, in which the pole piece is located at the first end of the chamber and the first port is located at the second end of the chamber.

13. The valve of claim 12, in which a recess is formed at the first end of the chamber, the recess having a circumferential edge that forms a seating surface having a curvature that matches the curvature of the plug.

14. The valve of claim 12, in which the driving means comprises a source of gas under pressure connected to the first port.

15. The valve of claim 7, in which the source of electric current comprises periodic pulses.

16. The valve of claim 7, in which the source of electric current comprises periodic pulses with a variable duty cycle.

17. The valve of claim 7, in which a recess is formed at the end of the chamber opposite the first port, the recess having a circumferential edge that forms a seating surface having a curvature that matches the curvature of the plug.

18. The valve of claim 14, in which the second port opens into the chamber intermediate the ends.

19. The valve of claim 10 in which the distance of travel of the plug between the ends of the chamber is less than about 0.03 times the diameter of the plug.

20. The valve of claim 10 additionally comprising means for adjusting the distance between the ends of the chamber.

21. The valve of claim 20 in which the chamber is formed as a bore in a valve body having a substantially larger diameter than the plug and the adjusting means comprises spaced apart end pieces at least one of which is axially adjustable within the bore to form the respective first end and second end of the chamber, the bore leaving the plug free to move between the ends of the chamber unguided.

* * * * *